(12) United States Patent
Korzhenko

(10) Patent No.: US 11,888,161 B2
(45) Date of Patent: Jan. 30, 2024

(54) COMPOSITION FOR BATTERY ELECTRODES

(71) Applicant: Arkema France, Colombes (FR)

(72) Inventor: Alexander Korzhenko, Lacq (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 17/773,731

(22) PCT Filed: Jun. 9, 2021

(86) PCT No.: PCT/FR2021/051037
§ 371 (c)(1),
(2) Date: May 2, 2022

(87) PCT Pub. No.: WO2021/250355
PCT Pub. Date: Dec. 16, 2021

(65) Prior Publication Data
US 2022/0376254 A1 Nov. 24, 2022

(30) Foreign Application Priority Data
Jun. 12, 2020 (FR) ...................................... 2006147

(51) Int. Cl.
*H01M 4/62* (2006.01)
*H01M 4/04* (2006.01)
*H01M 4/583* (2010.01)

(52) U.S. Cl.
CPC ......... *H01M 4/621* (2013.01); *H01M 4/0404* (2013.01); *H01M 4/0435* (2013.01); *H01M 4/583* (2013.01)

(58) Field of Classification Search
None
See application file for complete search history.

(56) References Cited

U.S. PATENT DOCUMENTS 9,229,375 B2 1/2016 Kubo et al.
2018/0261402 A1* 9/2018 Manabe ............... B01J 13/0026

FOREIGN PATENT DOCUMENTS

EP 2479167 A1 7/2012

OTHER PUBLICATIONS

Ahmed et al., "Energy impact of cathode drying and solvent recovery during lithium-ion battery manufacturing", Journals of Power Sources, Elsevier, 2016, 46 pages.
International Search Report and Written Opinion for International Application No. PCT/FR2021/051037, dated Aug. 30, 2021, 7 pages.

* cited by examiner

*Primary Examiner* — Tracy M Dove
(74) *Attorney, Agent, or Firm* — RatnerPrestia

(57) ABSTRACT

The present invention relates to a composition for battery electrodes in which at least one solvent is a composition comprising between 80% and 95% by mass of N-methylpyrrolidone (NMP).

2 Claims, No Drawings

COMPOSITION FOR BATTERY ELECTRODES

CROSS-REFERENCE TO RELATED APPLICATIONS

This application is the U.S. national phase of International Application No. PCT/FR2021/051037, filed 9 Jun. 2021, which claims priority to French Application No. FR 2006147, filed 12 Jun. 2020, the disclosure of each of these applications being incorporated herein by reference in its entirety for all purposes.

FIELD OF THE INVENTION

The present invention relates to a composition for battery electrodes in which at least one solvent is a composition comprising between 80% and 95% by mass of N-methylpyrrolidone (NMP).

BACKGROUND OF THE INVENTION

Compositions for manufacturing battery electrodes (cathode and anode) are well known. They are composed of solvent, active material, an electron conductor (for example of carbon-based nature (carbon black, graphenes, carbon nanotubes, graphite or carbon fibers, alone or in combination)), a polymeric binder, or even other additives such as one or more polymeric or nonpolymeric dispersants.

Among the solvents used is NMP for its suitable properties (the capacity for dissolving the polymeric binder, and the very high autoignition temperature (270° C.) allowing the application of the composition and drying in the presence of air).

This solvent is generally recycled by distillation or double distillation so as to obtain a maximum degree of purity of NMP. This operation is directed toward limiting the consumption of NMP in the overall manufacturing process but, however, has an industrial cost. The electrode manufacturing processes known to date require an NMP purity level of at least 99% by mass. When recycling is not desired for cost reasons, the solvent is generally burned, which is an aberration.

To obtain a purity of at least 99% by mass or even more during the recycling operation, use is made, for example, of distillation techniques described in EP 2479167.

In the process for manufacturing battery electrodes, a composition is deposited on a current collector. This composition consists, for the main components, of solvent, electron conductor, active filler and polymers. The solvent is subsequently evaporated off to obtain the electrode. The recovery of this solvent does not make it possible to obtain a purity as is possible in the known distillation processes of EP 2479167, for example. This solvent recovered during the electrode manufacturing process may contain up to almost 20% of compounds other than pure solvent.

Hitherto, the industrial electrode manufacturing processes required purification of the solvent or the use of "fresh" solvent.

The Applicant has observed that, in the case of N-methylpyrrolidone, the re-use of this solvent derived from the process of evaporation in air during the electrode manufacturing step was not only possible without purification, but also presented numerous advantages:
the dispersions are better,
the formulations are more stable over time,
the electrodes manufactured are of better quality: more precisely, they have a better distribution of the carbon-based components in the electrodes. Thus, the electrical resistivity is improved.

This impure NMP has NMP contents of between 80% and 99% and preferably between 95% and 99%, water contents of less than or equal to 0.1%, and compounds derived from the preceding processes in which the NMP is used, typically compounds bearing γ-butyrolactam (2-pyrrolidone) or γ-butyrolactone species.

The presence of γ-butyrolactam or γ-butyrolactone species in the impurities might constitute dispersants or might become grafted onto the electron conductor, thus facilitating its distribution in the electrode. The Applicant has no explanation and considers this effect as unexpected.

Thus, by conserving certain compounds derived from preceding electrode manufacturing processes, not only is it possible to use such an NMP for the manufacture of battery electrode compositions, but also the qualities of the compositions obtained are higher.

The electrode and more particularly the cathode formulation based on such an NMP solvent, applied to the electrical current collector, undergoes drying in air at a temperature below the boiling point of NMP, typically below 220° C. under partial pressure. Under identical conditions of an electrode manufacturing process, the use of the NMP composition of the invention makes it possible to reduce the electrical resistance of the electrodes, which is a critical parameter of battery applications. Furthermore, the use of the composition of the invention makes it possible to simplify the formulation of the electrodes by reducing, for example, the amount of dispersing polymer and/or binder.

SUMMARY OF THE INVENTION

The invention relates to a composition comprising:
at least one solvent whose composition comprises N-methylpyrrolidone in mass contents of between 80% and 98.99%, limits inclusive, water in mass contents of less than 1% and at least one compound bearing at least one γ-butyrolactam or γ-butyrolactone ring, NMP excluded, each of these compounds being present in mass proportions ranging from 0.01% to 19%, limits inclusive, alone or in combination, the total of these compounds not exceeding 19%, said solvent being present in mass proportions of greater than or equal to 50%,
at least one electron conductor in solid form in proportions of less than or equal to 50%, 0 excluded.

DETAILED DESCRIPTION OF THE INVENTION

The compositions of the invention comprise less than 50% by mass of electron conductor in solid form, preferably less than 35%, preferentially less than 25%, more preferably less than 10% and more preferably less than 5% by mass.

The term "electron conductor in solid form" means carbon blacks, graphenes, single-walled or multi-walled carbon nanotubes, graphites and carbon fibers, alone or in combination. Preferably, the electron conductor comprises carbon nanotubes.

The compositions of the invention also comprise at least one compound bearing at least one pyrrolidone ring (γ-butyrolactam), NMP excluded, and/or γ-butyrolactone, each of these compounds being present in proportions ranging from 0.01% to 19%, alone or in combination, the total of these compounds not exceeding 19%.

The term "compound bearing at least one pyrrolidone ring (γ-butyrolactam) or γ-butyrolactone" may refer to any compound with a molecular weight of less than 15 000 g/mol, preferably less than 10 000 g/mol, and in which the presence of a γ-butyrolactone or γ-butyrolactam ring is characterized (mass spectroscopy, NMR or infrared spectroscopy).

The γ-butyrolactone and γ-butyrolactam structures may bear substituents comprising C, H, N or O.

Among these compounds are γ-butyrolactone, succinimides such as N-methylsuccinimide and N-hydroxysuccinimide, formylpyrrolidone, 5-hydroxy-N-methylpyrrolidone, 2-pyrrolidone, or N-hydroxymethylpyrrolidone, among the main ones. They may also be oligomers bearing a γ-butyrolactam and/or γ-butyrolactone ring of a form that is more or less complex or difficult to characterize as regards either their nature or their concentration.

It is considered that all the impurities derived from the γ-butyrolactam or γ-butyrolactone structure present in the solvent derived from evaporation during the electrode manufacturing process may be present in the compositions of the invention. Lighter compounds whose structure does not comprise a γ-butyrolactam or γ-butyrolactone structure may also be found.

Preferably, these compounds are present in contents of between 0.01% to 19% by mass, more preferably between 0.1% and 10% and more preferably between 0.5% and 5% by mass, limits inclusive.

This solvent composition is obtained by recovering NMP vapors in the presence of air for temperatures above 120°.

This solvent composition may also be obtained by purposely adding γ-butyrolactam and/or γ-butyrolactone derivatives to NMP whose purity is greater than 99%, although this is not the prime objective of the invention, which uses NMP without the need for purification, thus containing these γ-butyrolactone and/or γ-butyrolactam compounds.

The compositions of the invention may also comprise an active filler. The term "active filler" means lithiated transition metal oxides such as $LiMO_2$, of the $LiMPO_4$ type, of the $Li_2MPO_3F$ type or of the $Li_2MSiO_4$ type in which M is Co, Ni, Mn, Fe or a combination thereof, of the $LiMn_2O_4$ type or of the $S_8$ type, artificial or natural graphites or silicon or silicon modified with carbide, nitrides or oxides.

The compositions of the invention may also comprise one or more polymers, chosen from poly(vinylidene fluoride) (PVDF) polymers, poly(vinylpyrrolidone), poly(phenylacetylene), poly(meta-phenylenevinylidene), polypyrrole, poly(para-phenylenebenzobisoxazole), poly(vinyl alcohol), carboxymethylcellulose and mixtures thereof, and polyacrylonitrile and copolymers thereof. Preferably, it is poly(vinylidene fluoride) (PVDF) and poly(N-vinylpyrrolidone).

The compositions of the invention may also comprise one or more free-radical generators, such as peroxides, redox couples, azo compounds or alkoxyamines, alone or in combination in contents of less than 5% and preferably less than 1% by mass relative to the NMP.

The invention also relates to a process for obtaining an electrode, comprising the following steps:
deposition of the composition of the invention comprising at least one active filler, at least one polymer on an electrical current collector,
evaporating off the solvent,
optionally calendering.

The invention also relates to a process for obtaining an electrode, in which the solvent recovered by evaporation comprises the solvent of the invention.

The metallic electrical current collector is chosen from the following metals: Al, Cu, Ni in a nonlimiting manner, and has a thickness of between 8 and 35 µm. The metallic collector may also be coated with a primer deposited on the electron conductor in a thickness of between 0.5 and 5 µm.

The calendering consists in compressing the electrode between two counter-rotating rolls, in which the gap between the rolls is less than the thickness of the electrode.

The electrode may be a cathode or an anode. Preferably, it is a cathode.

For the cathodes, the active material is chosen from lithiated transition metal oxides such as $LiMO_2$, of the $LiMPO_4$ type, of the $Li_2MPO_3F$ type, of the $Li_2MSiO_4$ type, where M is Co, Ni, Mn, Fe or a combination thereof, of the $LiMn_2O_4$ type or of the $S_8$ type.

For the anodes, the active material is chosen from artificial or natural graphites or silicon or silicon modified with carbide, nitrides or oxides.

The invention also relates to a battery using a cathode and/or an anode obtained according to the process of the invention.

The invention also relates to the use of the compositions of the invention in fields such as inks and paints, or in petroleum extraction.

The formulation of the electrode (cathode or anode) may be as follows, in a nonlimiting manner:
a solids content of between 20% and 90% by mass, the remainder being the solvent (composition comprising N-methylpyrrolidone in mass contents of between 80% and 98.99%, limits inclusive, water in mass contents of less than 1% and at least one compound bearing at least one γ-butyrolactam or γ-butyrolactone ring, NMP excluded, each of these compounds being present in mass proportions ranging from 0.01% to 19%, limits inclusive, alone or in combination, the total of these compounds not exceeding 19%),
one or more electron conductors in proportions of between 0.1% and 5% of the total formulation for manufacturing the electrode,
polymeric or nonpolymeric additives (binder, dispersant) in proportions of between 0.3-5% of the total formulation for manufacturing the electrode.

Example 1

Preparation of the dispersion of Graphistrength® C100 HP carbon nanotubes in electronic-grade NMP solvent (reference).

Graphistrength® C100 HP CNT is the commercial grade from Arkema containing <20 ppm of metallic impurities. This grade of purified CNTs is recommended for use in the cathodes of Li-ion batteries. These carbon nanotubes are multi-walled (between 10 and 15 walls) and their specific surface area is between 180 and 240 $cm^2/g$.

Preparation of the Dispersion:

100 g of Graphistrength® C100 HP in powder form are premixed with 400 g of NMP (electronic grade, purity >99.8% by mass), using a deflocculator equipped with a 55 mm paddle.

25 g of PVP K 30 (BASF) are added gradually over one hour with stirring at 1000-1600 rpm.

A further 70 g of NMP are added after 30 minutes, and a further 65 g of NMP are added 30 minutes later.

The predispersion in an amount of 660 g, containing 15% of CNT and 3.8% of PVP, is ready for the step of milling in a Brandt horizontal ball mill (HBM), with a mill chamber volume of 250 ml.

The mill is charged with 180 ml of ceramic beads with a diameter of 0.4-0.7 mm and the gap size is 0.1-0.15 mm.

The milling circuit is primed with 230 g of NMP alone for 5 minutes.

The predispersion is gradually added over 15-20 minutes, while increasing the rotor speed to 3000 rpm and the pump to 35% of the capacity.

Solids content and absorbance measurements were taken to monitor the evolution of the dispersion (table 1).

TABLE 1

| Time in minutes | Solids content % | Mass % CNT | Absorbance at 50 ppm CNT |
|---|---|---|---|
| 0 | 8.55 | 6.84 | 0.931 |
| 10 | 8.54 | 6.83 | 1.498 |
| 40 | 8.7 | 6.96 | 2.617 |
| 70 | 8.67 | 6.94 | 2.895 |
| 120 | 8.78 | 7.02 | 3.378 |
| 200 | 9.37 | 7.50 | 3.442 |
| 260 | 8.22 | 6.58 | 3.434 |
| Addition of NMP to target 4% of CNT | | | |
| 320 | 4.93 | 3.94 | 3.346 |

For each absorbance measurement, the dispersion taken from the mill was diluted to 50 ppm of CNT. It was measured using a DR/2000 spectrometer (Hach) at a wavelength of 355 nm.

Example 2: Recovery NMP and CNT Dispersion Based on this Solvent (Invention)

The NMP solvent of example 1, of "electronic" grade, was used to prepare the typical "cathode" formulation for the Li battery. For 960 g of NMC 622 produced by Umicore (LiNi$_{0.6}$Mn$_{0.2}$Co$_{0.2}$O$_2$), 20 g of Kynar® HSV 1810 PVDF produced by Arkema were added. The dry premix was dispersed in 1950 ml of NMP using a disc mixer for 30 minutes. 50 g of the CNT dispersion of example 1 were then added. The solvent was overdosed relative to the formulations used in the production of the cathodes since the purpose of this example is to model the recovery of the solvent in the presence of the typical ingredients of a cathode.

The dispersion was placed in a 5 l Lab Rotovap brand rotary evaporator. The evaporator was heated to 145° C. and the condensate vessel was maintained at 110° C. The condenser vacuum valve was kept open to maintain the contact of the NMP condensate with the air.

Over 24 hours, 900 g of solvent with a pronounced yellow color were recovered in the vessel.

The recovered NMP was analyzed by the Karl Fischer method for the presence of water, the value obtained being 650 ppm. The NMP purity amount of 94.6% was obtained by mass spectroscopy. Thus, about 5% of recovered NMP may be attributed to the nonvolatile NMP oxidation products.

This recovery NMP sample was used to prepare the CNT dispersion according to the method described in example 1, adhering to the same conditions.

Solids content and absorbance measurements were taken to monitor the evolution of the dispersion (table 2).

TABLE 2

| Times in minutes | % Solids content | Mass % CNT | Absorbance at 50 ppm CNT |
|---|---|---|---|
| 0 | 8.51 | 6.81 | 1.022 |
| 15 | 8.64 | 6.91 | 1.634 |
| 40 | 8.67 | 6.94 | 2.801 |
| 60 | 8.81 | 7.05 | 3.244 |
| 90 | 8.85 | 7.08 | 3.645 |
| 120 | 9.51 | 7.61 | 3.845 |
| Addition of NMP to target 4% of CNT | | | |
| 320 | 5.06 | 3.05 | 3.742 |

For the absorbance control, the recovery NMP was used for the reference cell. It is observed that the evolution of the dispersion is faster in the case of the recovery NMP. After 90 minutes of milling, the absorbance approaches saturation, which is observed after 120 minutes of milling in example 1. The absorbance value is higher in example 1, which may reflect a better performance of the dispersion of the invention.

Example 3: Electrical Performance of the CNT Dispersion of Examples 1 and 2 in the Cathode Formulation Preparation of the Cathode Formulation The solution of Kynar® HSV 1810 PVDF at 8% in "electronic" grade NMP in an amount of 12.5 g was mixed with the same amount of the CNT dispersion of example 1 using a disc mixer, at 400 rpm. After 15 minutes of mixing, 98.5 g of NMC 622 and a further 10 g of NMP are gradually added to maintain good fluidity of the dispersion. The objective for the viscosity is between 3500 and 5000 cPs. Mixing was complete after 30 minutes at 1500 rpm.

The dispersion was then applied to a polyethylene terephthalate (PET) support to a thickness of 100 μm using a doctor blade, targeting a coating thickness of 120 μm. The coating was dried in a ventilated oven for 30 minutes at 130° C.

The solids content of this "model" cathode formulation is as follows:

NMC: 98.5%; PVDF 1%; CNT 0.5%

The coated PET sheet is cut to obtain 3×4 cm samples. The ends of each sample are covered with a conductive ink containing silver. The electrical resistivity was measured using a Keithlley brand electrometer.

The same protocol was applied to obtain a cathode model with the CNT dispersion of example 2. The results of the electrical measurements are summarized in Table 3.

TABLE 3

| | NMP purity in the CNT dispersion | Dispersion quality measured by absorbance | Electrode (cathode) resistivity Ohm · cm |
|---|---|---|---|
| example comparative NMP | >99% | 3.346 | 62 |
| Example composition invention, recovery | >94.6% | 3.742 | 39 |

Under similar conditions, the CNT dispersion prepared based on recovery NMP demonstrates better electrical performance in the NMC622 cathode type formulation, the resistivity of the electrode is lower, which is favorable to the correct functioning of a battery.

The invention claimed is:

1. A process for obtaining an electrode, comprising:
   depositing a composition onto an electrical current collector,
   wherein the composition comprises:
   at least one solvent comprising:
   N-methylpyrrolidone (NMP) in a amount of between 80% and 98.99% by mass, limits inclusive;
   water in an amount of less than 1% by mass; and
   at least one compound bearing at least one y-butyrolactam or y-butyrolactone ring, NMP excluded, where the at least one compound is present in an amount ranging from 0.01% to 19% by mass, limits inclusive,
   wherein the at least one solvent is present in an amount of greater than or equal to 50% by mass relative to the composition, and is obtained by recovering NMP vapors in the presence of air at temperatures above 120° C.;
   at least one electron conductor in solid form in an amount of greater than 0 but less than or equal to 50% by mass relative to the composition;
   an active filler; and
   at least one polymer, and
   evaporating off the at least one solvent.

2. The process as claimed in claim 1, wherein the composition further comprising a free-radical generator.

* * * * *